(12) United States Patent
Ruffieux et al.

(10) Patent No.: US 7,611,008 B2
(45) Date of Patent: Nov. 3, 2009

(54) PACKAGE FOR A MEDICAL ANCHOR ELEMENT AND SUTURE THREAD

(75) Inventors: Kurt Ruffieux, Thalwil (CH); Heiner Kern, Seuzach (CH); Dennis Reichardt, Zurich (CH); Alexander Siegrist, Wettswil a. A. (CH)

(73) Assignee: Karl Storz GmbH & Co. KG (DE)

( * ) Notice: Subject to any disclaimer, the term of this patent is extended or adjusted under 35 U.S.C. 154(b) by 178 days.

(21) Appl. No.: 11/673,174

(22) Filed: Feb. 9, 2007

(65) Prior Publication Data

US 2007/0235359 A1 Oct. 11, 2007

(30) Foreign Application Priority Data

Feb. 10, 2006 (DE) .................. 10 2006 007 263

(51) Int. Cl.
*A61B 17/06* (2006.01)
(52) U.S. Cl. ..................... 206/63.3; 206/339
(58) Field of Classification Search ............... 206/63.3, 206/33, 339, 438, 439, 363, 370
See application file for complete search history.

(56) References Cited

U.S. PATENT DOCUMENTS

| 1,962,900 | A | * | 6/1934 | Hirsch ................ 206/63.3 |
| 4,632,100 | A | * | 12/1986 | Somers et al. ............ 606/232 |
| 4,700,833 | A | * | 10/1987 | Smith ................ 206/380 |
| 5,078,730 | A | | 1/1992 | Li et al. ............ 606/228 |
| 5,174,087 | A | * | 12/1992 | Bruno ................ 53/430 |
| 5,358,624 | A | * | 10/1994 | Roshdy et al. ........... 206/363 |
| 5,468,252 | A | * | 11/1995 | Kaplan et al. ........... 606/228 |
| 5,487,469 | A | * | 1/1996 | Roshdy et al. ........... 206/363 |
| 5,690,676 | A | | 11/1997 | DiPoto et al. ............ 606/232 |
| 5,715,942 | A | | 2/1998 | Li et al. ............ 206/339 |
| 5,788,063 | A | * | 8/1998 | Van Ness ............ 206/63.3 |
| 5,954,748 | A | | 9/1999 | Totakura ............ 606/229 |
| 6,080,184 | A | | 6/2000 | Peters et al. ............ 606/228 |
| 6,098,796 | A | * | 8/2000 | Januzeli et al. ............ 206/227 |
| 6,139,565 | A | | 10/2000 | Stone et al. ............ 606/232 |
| 6,241,734 | B1 | * | 6/2001 | Scribner et al. ............ 606/93 |
| 6,260,699 | B1 | * | 7/2001 | Kaplan et al. ............ 206/339 |
| 6,409,016 | B1 | * | 6/2002 | Braginsky et al. ........... 206/397 |
| 6,613,054 | B2 | * | 9/2003 | Scribner et al. ............ 606/93 |
| 6,719,128 | B2 | * | 4/2004 | Alpern et al. ............ 206/63.3 |
| 2001/0004966 | A1 | * | 6/2001 | Warnecke ............ 206/63.3 |

(Continued)

FOREIGN PATENT DOCUMENTS

EP 0 717 958 6/1996

OTHER PUBLICATIONS

European Search Report, May 4, 2007, 2 pages.

*Primary Examiner*—Ehud Gartenberg
*Assistant Examiner*—King M Chu
(74) *Attorney, Agent, or Firm*—St. Onge Steward Johnston & Reens LLC (57) ABSTRACT

A package is used for the packaging of an anchor element together with a suture thread which is threaded on the latter. It is proposed to provide the package with an outer casing hermetically closed to the outside, the casing container holder which receives said anchor element and which has a seat for the suture thread already wound on the anchor element.

8 Claims, 4 Drawing Sheets

U.S. PATENT DOCUMENTS

| | | | |
|---|---|---|---|
| 2002/0175091 A1* | 11/2002 | Williamson et al. | 206/63.3 |
| 2003/0029737 A1* | 2/2003 | Alpern et al. | 206/63.3 |
| 2003/0178325 A1* | 9/2003 | Roshdy et al. | 206/63.3 |
| 2004/0050721 A1* | 3/2004 | Roby et al. | 206/63.3 |
| 2004/0124105 A1* | 7/2004 | Seiler et al. | 206/363 |
| 2005/0035007 A1* | 2/2005 | Kennedy et al. | 206/63.3 |
| 2005/0211588 A1* | 9/2005 | Kanner et al. | 206/380 |

* cited by examiner

PACKAGE FOR A MEDICAL ANCHOR ELEMENT AND SUTURE THREAD

BACKGROUND OF THE INVENTION

The invention relates to a package for an anchor element and a suture thread, said anchor element being able to be introduced with the suture thread into a bone for the purpose of fixing a tendon.

Anchor elements of this kind, also called suture thread anchors, are used in the medical field to ensure that tissues, mostly tendons, that have become detached from a bone can be fixed back onto the bone. For this purpose, the anchor element, into which a suture thread is threaded, is driven into the bone. The two suture thread ends are then tied onto the detached tendon and thus fix the latter back on the bone.

Different designs of anchor elements are known, for example those known from U.S. Pat. No. 4,632,100, U.S. Pat. No. 5,690,676 and U.S. Pat. No. 6,139,565.

Such an anchor element generally comprises an approximately cylindrical or pin-shaped body whose outer surface is provided with barb-like projections, and, after the anchor element has been driven into the bone, the barbs prevent it from being withdrawn from said bone. These barbs can also be designed as an outer thread, depending on the technique used to insert the anchor element. One technique involves forming a bore in the bone and striking or driving the anchor element into said bore. In another technique, without provision of a bore, the anchor element is turned in the manner of a screw into the bone or spongy substance. Depending on its design, the anchor element can be made of metal material, for example titanium, but designs made of bioabsorbable materials are also known.

A common feature of all these anchor elements is that they have to be connected to a tool in order to fit them in place, either with a kind of screwdriver or what is called a driver device.

For this purpose, a recess, for example in the shape of a hexagon, is usually provided at the proximal end of the anchor element, and a correspondingly shaped tool is pushed into the recess in order to fit the anchor element into the bone.

Since anchor elements of this kind are relatively small (lengths in the range of 1 to 1.5 cm and diameters in the range of 3 to 5 mm are common), this attachment to the tool requires a certain degree of attention and dexterity.

In addition, the anchor element is engaged onto a suture thread, for which purpose the anchor element has a transverse bore in its body or has suitable suture thread eyelets at the proximal end. Passing a suture thread through such a small body also requires a certain degree of attention and dexterity.

Since both the anchor element and the suture thread remain in the body after the surgical procedure, these structural elements have to be sterile in order to avoid infections. During the actual operation, the assembly made up of tool, anchor and suture thread is made ready by a surgical assistant in most cases. To do this, as has been mentioned, the tool is pushed into the proximal end of the anchor element. The suture thread, which was either already threaded in place beforehand or has now been threaded on, is guided along the tool to the proximal end and is secured there on radially projecting pins, to ensure that the suture thread does not move around and impede the insertion procedure.

It is an object of the invention to make this preparatory work easier and also to ensure sterile handling during these maneuvers.

SUMMARY OF THE INVENTION

According to the invention, this object is achieved, with a package for an anchor element and a suture thread, by the fact that the package comprises an outer casing, with a holder which is arranged inside the casing and in which an anchor element is received, and with a seat for the suture thread already threaded on the anchor element.

This measure has the advantage that an assembly made up of anchor element and suture thread is already in a packaged form, i.e. this assembly of anchor element and suture thread has already been prepared at the time of manufacture. This not only makes handling easier, since the threading-in procedure is dispensed with, it also makes it possible for these two structural elements remaining in the body to be jointly sterilized.

The fact that the anchor element is received in a holder means that, in the subsequent maneuvering stages, that is to say during production of the package and subsequently upon opening of the package, this element no longer needs to be touched, with the result that it can be kept sterile. The provision of a seat for the suture thread already threaded onto the anchor element affords the possibility of stowing the suture thread which is in fact often relatively long compared to the anchor element. Customary lengths for the two suture thread ends protruding from the anchor element are in the range of 20 to 30 cm, such that, compared to the small anchor element body, the suture thread takes up a relatively large amount of space. The receiving seat now opens up the possibility of arranging or stowing the suture thread there in a defined pattern that saves space.

This assembly made up of holder, anchor element and suture thread can be produced as a sterile assembly, which is then provided with an outer casing that closes this sterile assembly off from the outside. In this state, the package can now be dispatched from the original manufacturer and kept in stock in hospitals or general practices.

To prepare for the surgical intervention, the package is taken hold of and the outer casing is opened, after which it is possible to access the sterile components, namely the anchor element and the suture thread already engaged on the latter. The provision of a holder allows that the anchor element and the suture thread do not have to be gripped directly during the subsequent handling, and instead they can be gripped via the holder, with the result that their sterile state can be maintained, while the anchor element is connected to the tool. This opens up the possibility of then removing the suture thread from the seat, fixing it to the tool, and then finally withdrawing this assembly of tool, anchor element and suture thread from the holder and bringing it to the operating site. The tool used for handling can be a reusable tool, which is economic. After use, the tool can be sterilized and used again.

Handling is not only made easier by this, it can also be done in a sterile state.

In a further embodiment of the invention, the anchor element is received in a defined position in the holder.

This measure has the advantage that the person handling it knows exactly which orientation the anchor element is received in the holder, and this greatly facilitates the subsequent maneuvering and handling.

In a further embodiment, the anchor element is received in the holder in such a way that a tool for handling can be applied to the anchor element.

This measure has the advantage that not only can the anchor element be held in a defined position, it can also at the same time be given a specific orientation which is such that, even with the anchor element still held in the holder, the tool can be brought up to it and, depending on its design, fitted onto it or pushed into it. Thus, these maneuvers are not only made easier, they can also be carried out while a sterile state is maintained, and without its being necessary to grip the anchor element during these maneuvers.

In a further embodiment of the invention, the holder is designed as a handle.

This measure has the considerable advantage that, in order to facilitate the aforementioned maneuvers for attaching the tool to the anchor element, the holder can be gripped in one hand by the person handling it and can be brought into a suitable orientation, while the other hand applies the tool. This combination makes handling much easier and allows these maneuvers to be carried out in a sterile state.

In a further embodiment of the invention, the holder at the same time carries the suture thread.

This measure has the advantage that a very compact assembly is obtained, since the holder also serves at the same time as a seat for the suture thread. This assembly made up of holder, suture thread and anchor element can thus be suitably handled without the need for relative displacements between the anchor element and the suture thread. It is only after the tool has been pushed into or fitted onto the anchor element that the suture thread needs to be moved in order to fix it to the tool.

In a further embodiment of the invention, the anchor element and holder are connected captively to one another, but in a detachable manner.

This measure has the advantage that the anchor element is held captive in the holder, such that, during the above-described handling, there is no danger of the anchor element accidentally coming loose from the holder, for example falling out of the latter. By means of the possibility of detachment, this connection can be undone after the tool has been applied to the anchor element and pushed into it.

In a further embodiment of the invention, the holder is designed as a blank.

This measure has the advantage that such a blank can be produced inexpensively, simply and in many varied formats that can have corresponding features, namely for the holder of the anchor element and the seat for the suture thread. The blank can be cut or punched out from a planar material. The material can be a paper material.

In a further embodiment of the invention, the blank is folded into an envelope-like body, in the interior of which the suture thread is received.

This measure has the advantage that the relatively long suture thread in the envelope can be arranged as a more or less ordered bundle or ball. For this purpose, during manufacture of the package, the suture thread can be applied to a surface of the blank, and another section can then be folded round it to form an envelope-like body. To remove the suture thread, this envelope can then easily be opened again and the suture thread can be removed without problem.

In a further embodiment of the invention, the blank has at least one flap into which the anchor element is inserted.

This measure has the advantage that the aforementioned defined positioning and exact orientation of the anchor element holder can easily be achieved by simple machining operations. The anchor element can simply be pushed into such a flap and held and also handled there. The blank itself permits handling with one hand, without any need to touch the anchor element fitted in the flap.

The flap is produced in a particularly simple way by punches being made in the blank.

Handling is made even easier if the flap has a predetermined break point.

This measure has the advantage that the flap is torn open in order to remove the anchor element. As was mentioned at the outset, the outer surface of the anchor element is provided with barb-like anchoring elements which permit insertion in one direction, for example into the bone substance, and provide blocking in the opposite direction. By suitable shaping of the flap, it is now possible to first push the anchor element into the flap, while removal is blocked because of this barb-like design. By means of the predetermined break point, the flap can now simply be torn open to permit removal. On the one hand this ensures a particularly secure hold of the anchor element on the holder, while on the other hand also ensures that the anchor element can be removed from the holder without any danger of relative displacements taking place between anchor element and tool during this removal.

In a further embodiment of the invention, the seat for the suture thread is designed as a wind-on body onto which the suture thread is wound.

This measure has the advantage that the suture thread is wound as a positionally defined structure around the body, such that there is no possibility of the two ends of the suture thread becoming entangled. The suture thread can accordingly be unwound again from the wind-on body, after the anchor element is fitted onto the tool.

In a further embodiment of the invention, the holder is designed as a wind-on card, onto which the anchor element can additionally be integrally formed.

If, for example, the anchor element is made of plastic material, these measures have the advantage that the holder and the anchor element can be produced in a single injection-molding operation. The suture thread can then be applied to or threaded into or wound onto this injection-molded assembly of holder and anchor element. After the tool has been applied and the suture thread unwound, a lateral tilting movement allows the anchor element to be broken off from the wind-on card, for which purpose the anchor element is connected to the wind-on card only via fine material webs, which then constitute predetermined break points.

In a further embodiment of the invention, the holder is designed as a bobbin body onto whose bobbin the suture thread is wound. In addition, the anchor element can be inserted into the hub opening of the bobbin body.

These measures have the advantage that, on the one hand, the suture thread is wound on in a very defined manner and can accordingly be easily unwound, and also that, by fitting the anchor element into the central hub opening, a very small, compact assembly and a correspondingly small package is obtained.

In a further embodiment of the invention, the holder is designed as a tubular body in whose interior the anchor element and the suture thread are received.

This measure has the advantage of providing a slender body into which the anchor element and the suture thread can be pushed. The tubular body can, for example, have a clear internal diameter approximately corresponding to the external diameter of the anchor element, such that the latter can be introduced into this body and be held by the latter, and so the holder at the same time constitutes a casing. If, for example, the anchor element is pushed into the tubular body such that its proximal end comes to lie at one end of the tubular body, the corresponding opening possibility can be provided there, such that, after opening, the tool can be applied, for which purpose the package in the form of the tubular body can still be held in the hand. The anchor element and suture thread are then withdrawn from the tubular body.

It will be appreciated that the aforementioned features and the features still to be explained below can be used not only in the cited combinations, but also in other combinations or singly, without departing from the scope of the present invention.

BRIEF DESCRIPTION OF THE DRAWINGS

The invention is described and explained in more detail below on the basis of a number of illustrative embodiments and with reference to the attached drawings, in which.

DETAILED DESCRIPTION OF PREFERRED EMBODIMENTS

Figure 1:
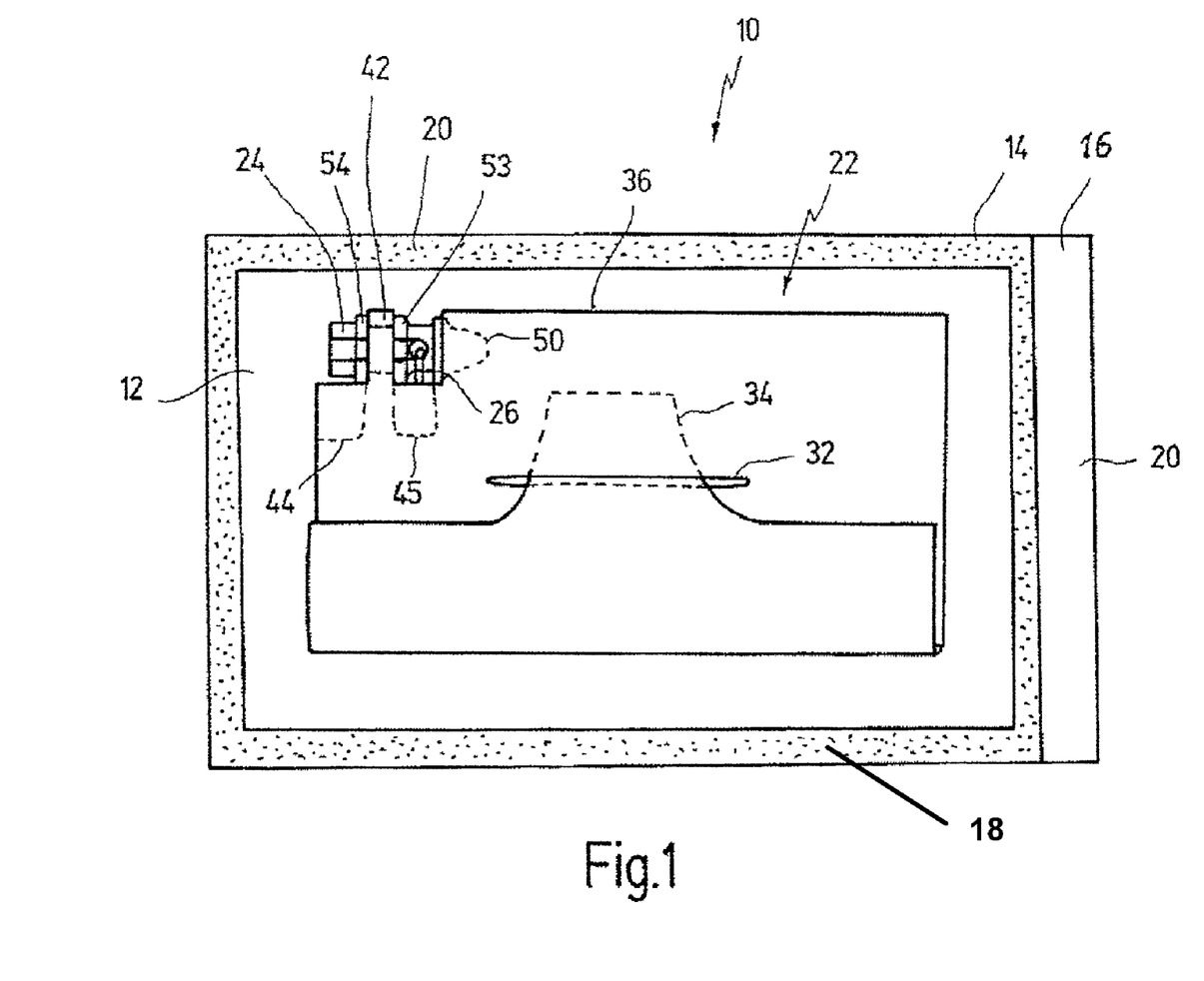
FIG. 1 shows a side view of a first illustrative embodiment of a package according to the invention.
Figure 2:
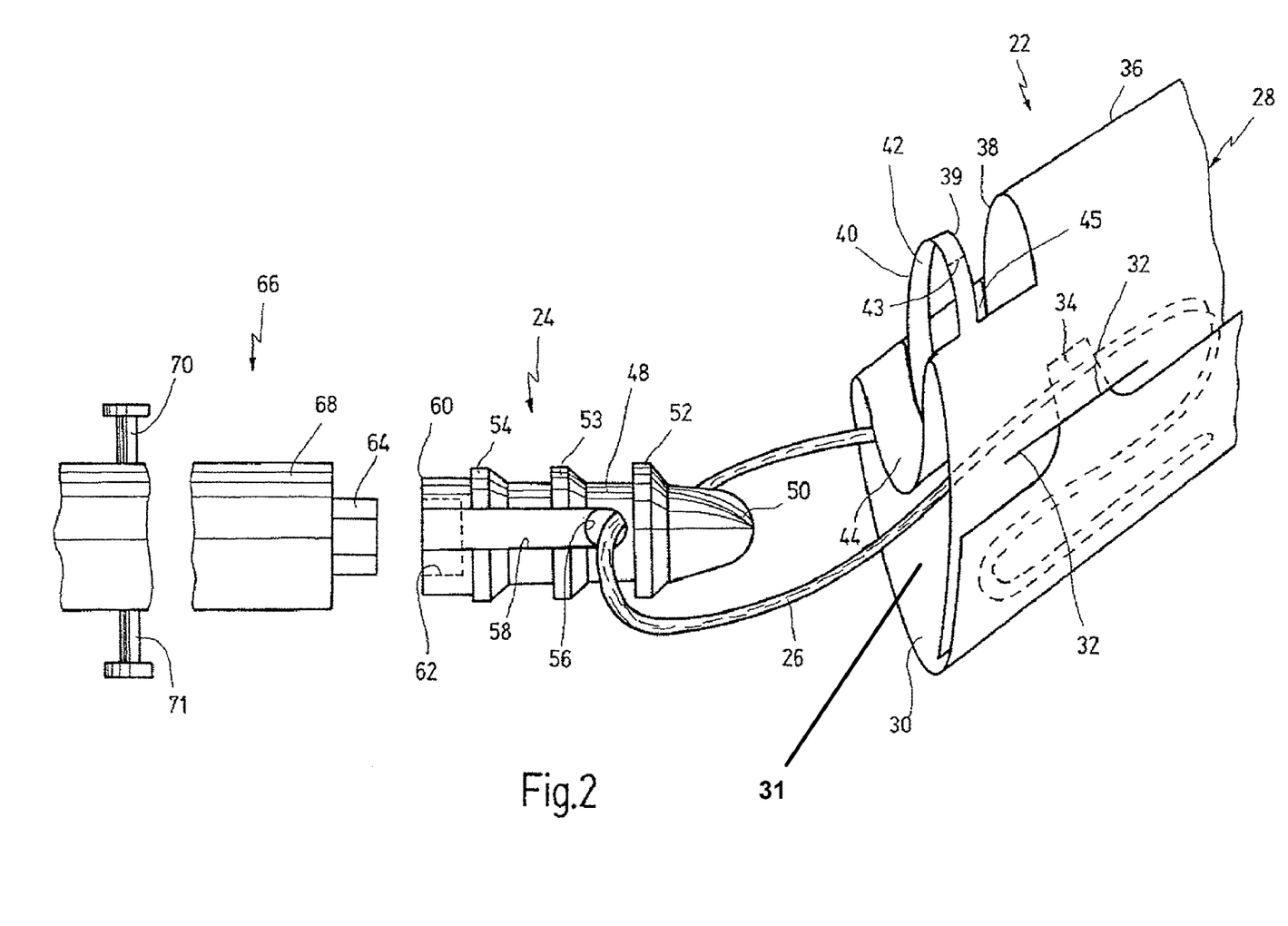
FIG. 2 shows a partial perspective view of the package from FIG. 1 after removal of the outer casing during a stage of the handling procedure.

In FIGS. 1 and 2, a first illustrative embodiment of a package according to the invention is designated in its entirety by reference number 10.

The package 10 has an outer casing 12 which is constructed from two superposed rectangular films 14 and 16 to form a pocket, by means of the two films 14, 16 being connected to one another by a peripheral adhesive joint 18.

The rectangular film 16 protrudes slightly beyond the other film 14 on one of the short sides of the rectangle, as a result of which a protruding flap 20 is formed which makes it easier to tear open the outer casing 12. For this purpose, the adhesive joint 18 is designed as an adhesive seal that connects the two films 14 and 16 to form a casing hermetically closed off from the outside, but which allows the two films 14 and 16 to be peeled off from one another in order to open the casing. The films themselves are made from plastic-coated aluminum films.

Arranged in the interior of the outer casing 12 there is a holder 22 which supports an anchor element 24 and a suture thread 26 connected to the anchor element 24.

The holder 22 is produced from a paper blank 28 which is punched and folded in such a way as to form an envelope 30 in the manner of an envelope for letters.

For this purpose, one side of the blank 28 is provided with a slit 32 into which a tuck-in tab 34 can be inserted, so as to form the aforementioned envelope 30.

In the area of the upper fold edge 36 in the view in FIGS. 1 and 2, three punch cuts 38, 39 and 40 are made so as to form a flap 42, the paper material being pressed inward on both sides in the form of pockets 44 and 45. As will be seen in particular from FIG. 2, the flap 42 is provided with a predetermined break point 43, which can also be applied during the punching operation.

As will be seen in particular from FIG. 1, these design measures serve to support the anchor element 24 in a defined position.

As will be seen in particular from FIG. 2, the anchor element 24 has an approximately cylindrical body 48 which merges at the distal end into a point 50.

On its outer face, the body 48 is provided with three hooks 52, 53 and 54 which are designed in the manner of annular flanges, and these each merge into the body 48 via a bevel oriented in the direction of the point 50. At the opposite end, the hooks 42 merge into the body 48 via a relatively straight undercut or step. In the area between the hooks 52 and 53, a transverse opening 56 is provided which extends right through the body 48 and through which a suture thread 26 is threaded, specifically in such a way that suture thread halves of approximately the same length come to lie on both sides of the opening 56. In the outer surface of the body 48, starting from the opening 56 and extending as far as the proximal end 60, notches 58 arranged diametrically opposite one another extend as far as the proximal end 60 and open out there. These notches 58 are used to guide the suture thread within the notches 58 along the body 48 from the opening 56 to the proximal end.

In the area of the end 60, the body 48 is provided with a recess 62, for example of hexagonal cross section.

This recess 62 is used to receive a correspondingly shaped projection 64 of a tool 66, in this case a driver device. This means that the projection 64 has a corresponding hexagonal cross section that corresponds to that of the recess 62.

The tool 66 is designed as a rod-shaped body 68 with a shaft (not shown here) and a handgrip, and two stubs 70 and 71 protrude radially from the rod-shaped body 68 at an axial distance from the projection 64, for example at a distance of 10 to 15 cm.

The two ends of the suture thread are wound around these stubs after the projection 64 has been pushed into the recess 62.

In FIG. 2, simply for the purpose of explaining the construction of the anchor element 24, the latter is shown already removed from the holder 22, in order also to demonstrate, among other things, how the two ends of the suture thread 26 are received in the inside of the blank 28 that has been folded to form an envelope 30. For explanatory purposes, the figure also shows the projection 64 not yet pushed into the recess 62.

It will also be seen from FIG. 2, in conjunction with FIG. 1, that the distance between the two hooks 53 and 54 corresponds approximately to the width of the flap 42.

It will be seen from FIG. 1 that the anchor element 24 is inserted sideways into the holder 22 in such a way that the flap 42 comes to lie between these two hooks 53 and 54. Insertion is made easier by the fact that the hooks are beveled in this direction, and withdrawal or accidental falling-out is prevented by the undercut or shoulder at the proximal end of the hooks 53, 54.

To manufacture the package 10, the blank is punched out, the suture thread 26 onto which the anchor element 24 is already engaged is placed in the envelope 30, the latter is then closed by inserting the tuck-in flap 34 into the slit 32, and the anchor element 24 is pushed into the flap 42. The inside of the envelope 30 forms a seat 31 from which the suture thread 26 can easily be removed. This assembly can now be sterilized, or these structural parts can be sterilized before being assembled, in which case care must be taken to ensure that the folding and tucking-in take place in a suitably sterile state, for example also in an automated manner.

The assembly composed of the holder 22, of the anchor element 24 inserted therein, and of the suture thread 26, is now pushed into the interior of the outer casing 12 and the adhesive joint 18 is produced, for example by heat-bonding or the like. In this packaged state, shown in FIG. 1, the package 10 can now be transported and handled.

During the handling involved in preparing for a surgical intervention, the outer casing 12 is torn open and the holder 22, that is to say the envelope 30, is removed from the torn-open envelope. To do so, the person handling it can, for example, grip the envelope 30 via the right-hand outer end thereof.

By virtue of the fact that the anchor element 24 is in an exactly defined position and has been inserted into the envelope 30 such that its proximal end 60 with recess 62 protrudes from the upper left end, the person handling it can now use his other hand to apply the tool 66 to the recess 62 and push the projection 64 in. By means of a lateral tilting movement, the predetermined break point 43 of the flap 42 can now be broken open, and the assembly made up of tool 66 and anchor element 24 can be withdrawn from the seat 31 inside envelope 30, in which process the suture thread 26 already threaded in the anchor element 24 is also withdrawn. To make this easier, the tuck-in flap 34 can be removed from the slit 32 for example, and in this way the envelope 30 is opened. The two ends of the suture thread 26 are then wound around the stubs 70 and 71, after which the anchor element 24 is then ready for insertion into the bone.

Figure 3:
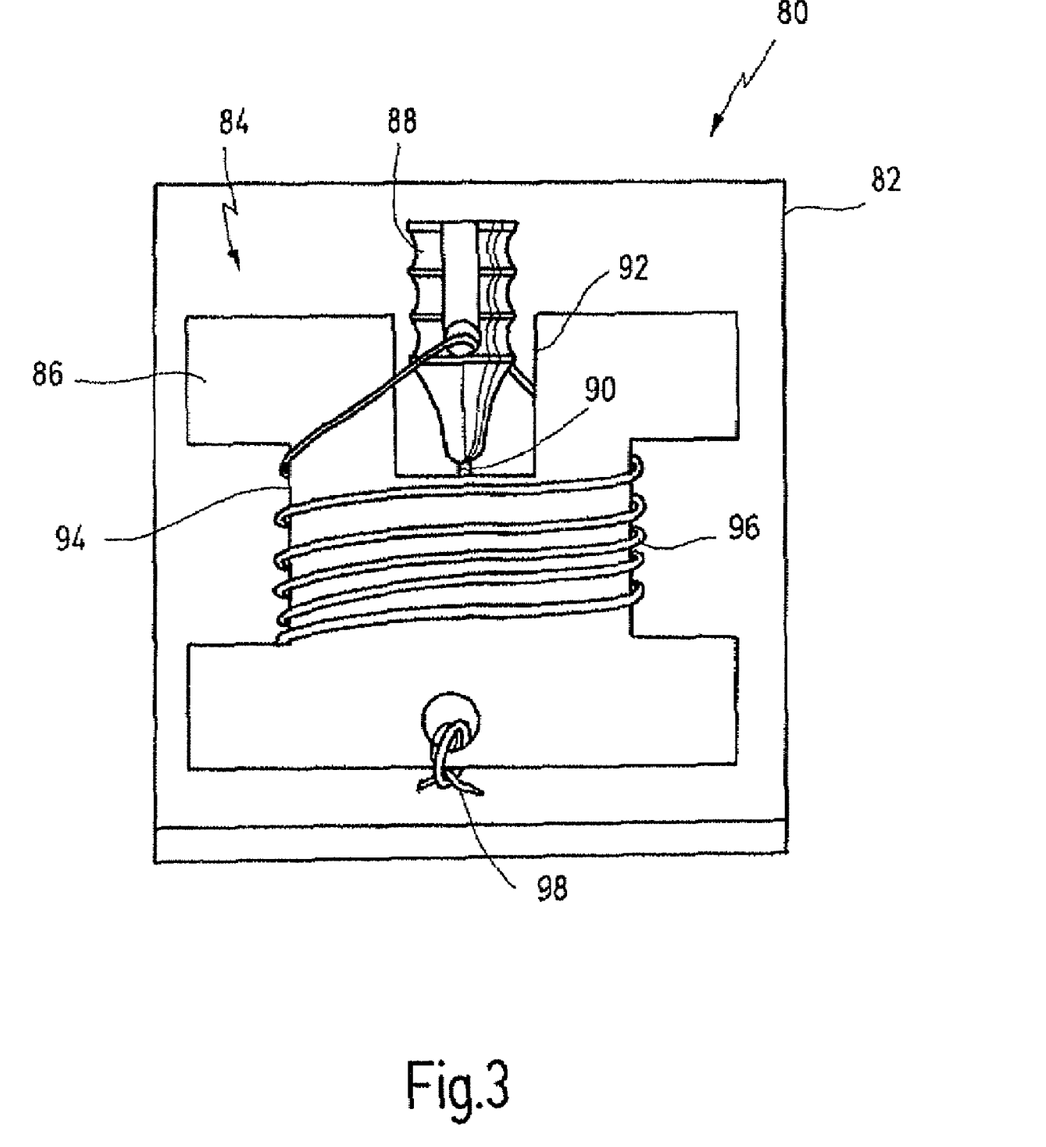
FIG. 3 shows a side view, comparable to the depiction in FIG. 4, of a second illustrative embodiment of a package according to the invention designed as a wind-on card with an anchor element formed integrally thereon.

In the second illustrative embodiment, shown in FIG. 3, the package according to the invention is designated in its entirety by reference number 80.

Here too, the package 80, as described above, has an outer casing 82, in the interior of which a holder 84 is received.

The outer casing 82 can be configured like the above-described outer casing 12.

The holder 84 is designed as a wind-on card 86 in the form of a plate-shaped plastic injection-molded body onto which the anchor element 88 is likewise molded as an injection-molded plastic part during the initial manufacturing process. For this purpose, the point of the anchor element 88 is securely connected to the wind-on card 86 by a web 90. In order to save space, a notch 92 is provided in which part of the body of the anchor element 88 comes to lie.

In the wind-on card 86, on both sides of a lengthwise edge, a notch-like narrowed area 94 is provided around which the suture thread 96 is wound or seated, and the latter is fixed in position by means of its end being connected to the wind-on card 86 via a knot 98.

In the manufacturing process, as has already been described, the wind-on card, with the anchor element formed integrally thereon, is first produced in an injection-molding operation. The suture thread 96 is then threaded through the anchor element 88 and, as described above, wound up and fixed. This assembly is also sterilized and is then inserted into the outer casing 82, and the latter is closed.

During the handling procedure, the outer casing 82 of the package 80 is again torn open, and the wind-on card 86 can be gripped by hand at a free end area and, as has been described above, the tool 66 can be pushed into or fitted on the anchor element 88. For this purpose, this proximal end of the anchor element 88 protrudes slightly from the wind-on card 86, in order to make this procedure easier. The suture thread 96 is now unwound and connected to the above-described stubs 70 and 71 of the tool 66. By means of lateral tilting away from the plane of the wind-on card, the web 90 is broken, such that the anchor element 88 along with the suture thread 96 can then be removed.

Figure 4:
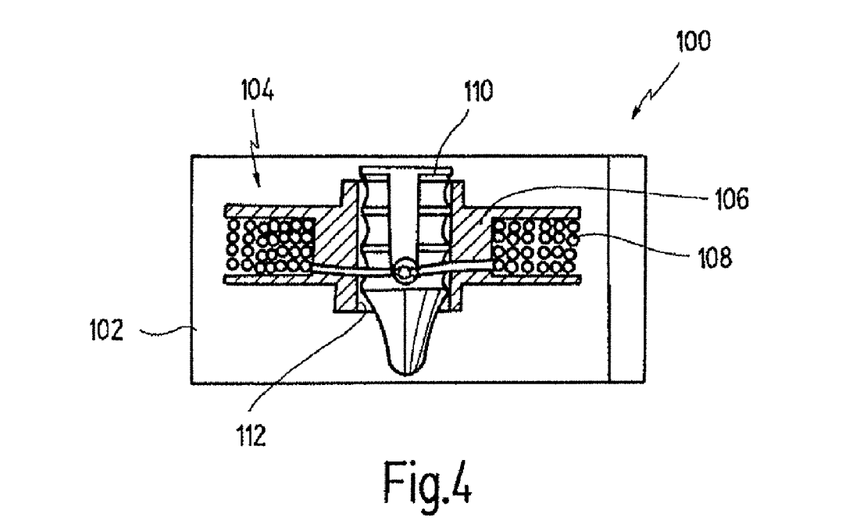
FIG. 4 shows a third illustrative embodiment, in partial section, in the form of a bobbin body with inserted anchor element.

FIG. 4 shows a third illustrative embodiment of a package 100 according to the invention. Here too, the package 100 has an outer casing 102 in the interior of which a holder in the form of a bobbin body 104 is received. The suture thread 108 is again wound or seated onto the actual bobbin 106 of the bobbin body 104. The anchor element 110, which is connected to the suture thread 108, is fitted into the hub opening 112 of the bobbin body 104. A particularly compact assembly is created here. The anchor element 110 is again fitted in such a way that the tool 66 can easily be pushed into its recess at the proximal end. In doing so, the holder in the form of the bobbin body is held by one hand. The suture thread is then unreeled and again connected to the stubs 70 and 71, after which the assembly is withdrawn from the bobbin body 104 and the latter is discarded.

Figure 5:
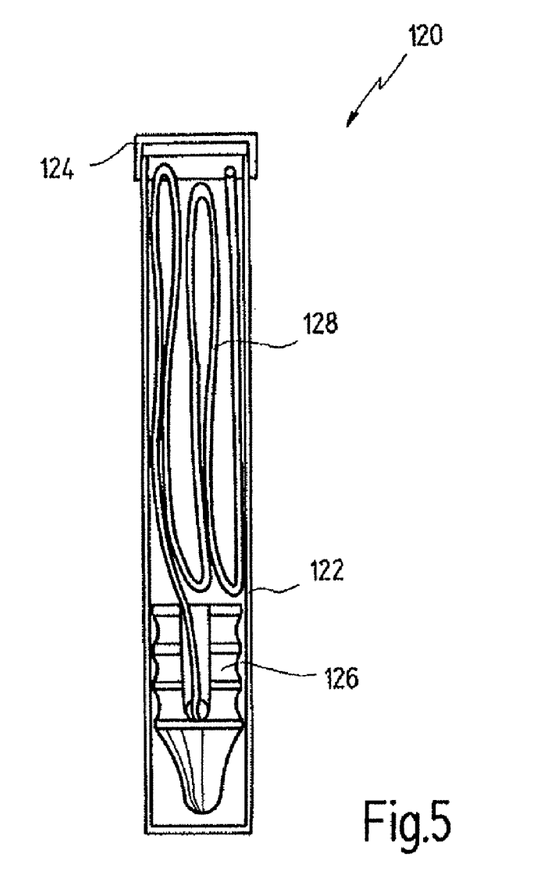
FIG. 5 shows a side view of a fourth illustrative embodiment of a package according to the invention with a tubular body.

FIG. 5 shows a fourth illustrative embodiment of a package 120 according to the invention.

The package 120 has a tubular body 122 which is closed at one end by a cap 124.

An anchor element 126, with a suture thread 128 engaged in the latter, is introduced into the tubular body. The clear internal diameter of the tubular body 122 corresponds to the external diameter of the anchor element 126, such that the latter can be introduced into the tubular body 122 and be safely guided and held therein. The package 120 can also be provided with an additional outer tear-open casing. However, the cap 124 can also be fitted directly onto it, such that the tubular body 122, with the cap 124 fitted thereon, then constitutes the outer casing.

During use, the cap 124 is removed and the assembly made up of suture thread 128 and anchor element is gradually withdrawn. Before the anchor element 126 is withdrawn completely from the tubular body 122, the tool can be pushed into the proximal end. For this purpose, given a suitably flexible design of the tubular body 122, the anchor element 126 can be briefly held in place by lateral pressing, and this procedure can also be done in a sterile state.

It is also possible for the anchor element shown at the lower end in FIG. 5 to be inserted in the reverse orientation and to provide a predetermined break point or corresponding cap at the lower end. Once again, after the cap has been removed, the tool can then first be fitted in place, and the assembly made up of anchor element 126 and suture thread 128 can then in this case, in the view in FIG. 5, be pulled downward out of the tubular body 122.

What is claimed is:

1. A package with an anchor element, having an approximately cylindrical body, together with suture thread, said anchor element can be introduced together with said suture thread into a bone for a purpose of fixing a tendon, having
   an outer casing hermetically closed off from an outside,
   a holder arranged inside said casing,
   said anchor element being received in said holder,
   a seat for said suture thread,
   said suture thread already threaded on said anchor element,
   wherein said holder is designed as a blank and wherein said blank has at least one flap into which said anchor element is inserted,
   wherein said flap has a predetermined break point,
   wherein said cylindrical body of said anchor element is provided with hooks on its outer face which are design in the manner of annular flanges, and
   wherein the distance between two hooks corresponds approximately to the width of said flap.

2. The package of claim 1, wherein said anchor element is received in a defined position in said holder.

3. The package of claim 1, wherein said anchor element is received in said holder in such a way, that after opening said outer casing, a tool for handling can be applied to said anchor element.

4. The package of claim 1, wherein said holder is designed as a handle.

5. The package of claim 1, wherein said holder provides said seat carrying said suture thread.

6. The package of claim 1, wherein said anchor element and said holder are connected captively to one another, but in a detachable manner.

7. The package of claim 1, wherein said blank is folded so as to form an envelope-like body, said suture thread being received in an interior of said envelope-like body.

8. The package of claim 1, wherein said flap is produced by punches made in said blank.

* * * * *